United States Patent [19]

Solly et al.

[11] Patent Number: 5,378,632

[45] Date of Patent: Jan. 3, 1995

[54] METHOD OF TESTING OILS

[75] Inventors: Richard K. Solly, Ascot Vale; Alan J. Power, Keilor; Ludek A. Beranek, Kooyong, all of Australia; Shiela J. Marshman, Woking, United Kingdom; Joanna F. Pedley, Walton on Thames, United Kingdom; Robin W. Hiley, Sevenoaks, United Kingdom

[73] Assignees: The Commonwealth of Australia, Australia; The Secretary of State for Defence in her Britannic Majesty's Government of the United Kingdom of Great Britain and Northern Ireland, United Kingdom

[21] Appl. No.: 849,058

[22] PCT Filed: Sep. 26, 1990

[86] PCT No.: PCT/AU90/00467

§ 371 Date: Apr. 24, 1992

§ 102(e) Date: Apr. 24, 1992

[87] PCT Pub. No.: WO91/05242

PCT Pub. Date: Apr. 18, 1991

[30] Foreign Application Priority Data

Sep. 27, 1989 [AU] Australia .................. PJ6614
Oct. 25, 1989 [GB] United Kingdom ............ 8924017

[51] Int. Cl.⁶ ................ G01N 21/78; G01N 33/28
[52] U.S. Cl. ...................... 436/60; 436/169; 436/171; 436/177; 208/46; 44/600
[58] Field of Search ............. 436/60, 161, 162, 164, 436/169, 177, 171; 208/46; 44/600, 903; 422/61

[56] References Cited

U.S. PATENT DOCUMENTS

| | | | |
|---|---|---|---|
| 4,181,597 | 1/1980 | Yan et al. | 208/46 |
| 4,556,326 | 12/1985 | Kitchen, III et al. | 374/45 |
| 5,059,303 | 10/1991 | Taylor et al. | 208/96 |
| 5,114,436 | 5/1992 | Reid | 44/385 |

FOREIGN PATENT DOCUMENTS

| | | |
|---|---|---|
| 93972 | 10/1970 | German Dem. Rep. |
| 207580 | 3/1984 | German Dem. Rep. |
| 1083479 | 9/1967 | United Kingdom |
| 1252299 | 11/1971 | United Kingdom |
| 85-120846/20 | 10/1984 | WIPO |
| 86-203691/31 | 12/1985 | WIPO |

OTHER PUBLICATIONS

Fuel "Storage Stability of Petroleum-Derived Diesel Fuel" vol. 67, Aug. 1988 pp. 1124–1130.
Fuel "Storage Stability of Petroleum-Derived Diesel Fuel" vol. 68, Jan. 1989, pp. 27–31.
ASTM Method "Standard Test Method For Oxidation Stability of Distillate Fuel Oil (Accelerated Method)" D 2274-88, pp. 123–127.
DEF STAN 05-50 "Methods for Testing Fuels, Lubricants and Associated Products Part 40: Storage Stability of Diesel Fuels" Issue 1, 2 Dec. 1987.

Primary Examiner—Nina Bhat
Attorney, Agent, or Firm—Merchant, Gould, Smith, Edell, Welter & Schmidt

[57] ABSTRACT

A method of testing oil for unstable reactive compounds include reacting unstable compound from an oil sample with an acid catalyst to form a reaction product, the color of which is then related to the presence and/or amount of reactive compound in the oil. Kits combining the necessary materials and reagents for performing the test method are also provided.

30 Claims, 2 Drawing Sheets

METHOD OF TESTING OILS

This invention relates to a method of testing oils for potential instability and to test kits for applying the test method.

Unstable oils undergo chemical degradation reactions which, over periods of time, produce small but insignificant changes in their properties. The amount of insoluble matter and/or sediment in the oil is one such property. These materials can plug the fuel channels in fuel filters and reduce or alter the spray pattern from engine injector nozzles. In both cases the required flow and delivery of fuel to the engine combustion chamber cannot be maintained and poor engine performance and possible mechanical damage may result.

Chemical reactions associated with unstable oils may also occur at an accelerated rate when the oil is heated. For example, hot metal components in fuel systems heat the fuel and may result in forming insoluble matter. This matter can form an organic deposit or varnish on such surfaces. The deposits may reduce the rate of heat exchange through the metal surface or alter the flow of fuel from those of the design requirements.

Concern with respect to the storage stability of oils is increasing as relative demand for the possible range of refinery product from crude oil has resulted in increased use of refinery cracking processes to convert part of the heavier ends to lighter middle distillate fuels. The cracked products, which contain higher amounts of chemically unstable species, are blended with more stable straight run streams to produce commercial fuels.

The strong influence of these unstable species in cracked refinery streams on deposit formation from the fuel is recognised by the oil industry, which frequently uses further refinery processing in the form of hydrogenation to reduce the concentration of these unstable species. Alternatively, or in addition, stabilizing additives may be added to the fuel which propose to reduce the extent of deposit formation.

The chemical reactions which produce insoluble materials in fuel are slow at ambient temperature and very little change can be detected even in a very unstable fuel during the short storage time at the refinery. It is believed that one important mechanism by which sediments are formed is reaction between trace compounds present in the oils to form solid or gummy products. Therefore even repeated filtration of the oils may not solve the problem of sediment formation. "Fuel" 67 (August 1988) 1124–1130 and 68 (January 1989) 27–31 suggest one of the principal reactions involved in sediment formation in diesel oils is the reaction between phenalanones (I) or Phenalenones (also known as perinaphthenones) (II), which are themselves produced by oxidation of phenalenes (also known as perinaphthalenes or benzonaphthenes) (III),

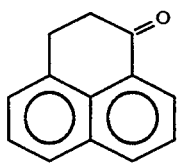

(I)

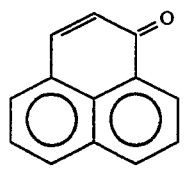

(II)

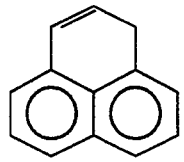

(III)

and indoles to form sediment precursor compounds of formula (IV) where R is alkyl and n is 1 to 3:

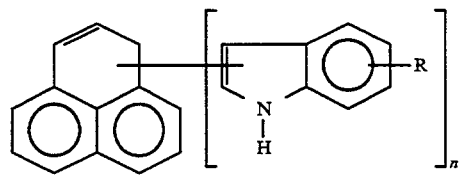

(IV)

In formula (I) to (IV), the tricyclic ring compounds may be substituted, for example by one or more alkyl groups. Phenalenes, phenalanones, phenalenones and indoles are believer to be introduced in the course of modifying the oils by incorporation of catalytically cracked oils.

The 1989 article describes reactions between synthesised phenalanones or phenalenones and indoles under acid conditions to yield intensely blue indolyl phenalene salts.

A number of methods have been developed to increase the rate at which deposits are formed so that meaningful amounts may be measured. The most common is the use of American Society for Testing and Materials (ASTM) Method D2274, which uses an elevated temperature of 95° C. for 16 hours and the bubbling of oxygen gas through the fuel. A recent experimental test method is to heat the fuel at 90° C. in an oxygen pressure bomb with an oxygen gas pressure of 794 kPa for 16 hours. This method is known as the oxygen overpressure test. Concern has arisen from those practising this art that the high temperatures and the presence of oxygen result in different chemical sediment producing reactions than occur at ambient temperatures. Gravimetric measurements of the amount of sediment produced under such conditions may not correlate with that produced on storage at ambient temperatures.

Much milder test conditions are found in the DEF STAN 05-50 (Part 40/1—long method) in which fuel (700 ml) is aged in a 1000 ml glass bottle for 28 days at 50° C. The gravimetric amount of sediment produced in this test is considered to give an approximation to the amount of sediment produced at 1 year of ambient storage and a good indication of the storage stability of a fuel. The long duration required to carry out this test makes it impractical for commercial decision making with respect to fuel stability prognostication.

The requirement for more rapid methods has lead to German (East) Patent DD 207580. Chromium (VI) is reduced by fuel in an aqueous medium and the change in light transmission in the medium measured at 460 nanometers. The amount of reduction of chromium (VI) is reported to be proportional to the oxidative stability of the fuel. The art of U.S. Pat. No. 4,556,326 is the measurement of the light transmission of a sample of fuel before and after it had been heated in the range 93° C. to 171° C. for from 3 minutes to 90 minutes.

It is the objective of this invention to provide a simple rapid alternative means to determine the relative stability of a fuel.

According to this invention there is provided a method of testing an oil for unstable reactive compounds characterised by contacting at least one said reactive compound from a sample of the oil with an acid catalyst to form a coloured reaction product, then relating the visible colour and/or colorimetric absorbance between 600–850 nm of this product to the presence and/or amount of unstable reactive compounds in the oil.

This method is applicable to oils which form sediments by reactions of polynuclear aromatic species and heteroaromatic species. The oils may be natural, e.g. petroleum oils or shale oils, or may be wholly or partly synthetic, e.g. prepared from natural gas, from coal or by heating shale, or in any other way. The term "oils" as used herein specifically includes petroleum spirit (gasolines), naphthas, paraffins (kerosine), distillate fuels such as tractor fuels, diesel fuels, gas oils and gas turbine fuels, lubricating oils, cutting oils and hydraulic oils. It is especially applicable to those oils in which sedimentation is a problem such as diesel fuels, gas oils and gas turbine fuels. It has been found to be applicable both to oils which are fresh from the refinery and which have been stored for a long time, for example several months.

The reactive compounds in the oil can be contacted with the acid catalyst in any suitable manner. For example, a sample of the oil may be added to the catalyst, or catalyst may be added to the oil sample. Various other materials which may be used to make the method of testing more sensitive and/or easier to operate are described below. The reactive compounds may be separated from the oil sample before they are contacted with the catalyst.

Although it is not limited to any specific scientific theory, it is believed that the test relies upon the oxidation of phenalenes by the oxidising agent to phenalenones, and the subsequent formation of a coloured indolylphenalene salt in the presence of acid. Such salts are generally blue to blue-violet in colour, but the colour formed if these potentially sediment-forming compounds are present may vary between blue and green, as there may also be yellow coloured compounds in the oil. The intensity of the colour is believed to be dependent upon the amount of potentially sediment-forming compounds in the oil. The colour may be observed by visually comparing the colour with a standard colour, for example by using a reference sample or colour chart, or by means of a colorimetric instrument. However the colour is observed, it may be related to the amount of these compounds in the oil, to the storage life of the oil or to its acceptability/non-acceptability for use, as is understood in the art. This may be done for example by initially testing an oil by both present methods and the method of the invention and preparing a calibration chart for subsequent use of the method of the invention.

The catalyst is any substance which has the properties of a Lowry-Bronsted acid or by reaction with the oil or solvent can form a Lowry-Bronsted acid, or can react directly with the nitrogen atom of an indole to form a salt.

Preferred acids are those which are colourless, and are known to form salts with the indolyl phenalenone condensation product. For example mineral acids such as hydrochloric or sulphuric and/or perchloric acid may be used and give a rapid colour formation. Preferred acids are organic sulphonic acids, such as alkyl or especially aryl sulphonic acids; for example, alkylphenyl sulphonic acids such as p-toluene sulphonic acid and napthalene sulphonic acid. Carboxylic acids such as acetic acid may be used but may give a slower reaction, a less intense colour and a less sensitive test. Preferred acid derivatives are aromatic or aliphatic acyl chlorides or acid anhydrides, such as benzoyl or acetyl chloride.

A rapid qualitative indication of the degree of stability of a fuel may be obtained by a visual inspection of the type and intensity of colour produced. A higher degree of quantification of the relative instability is obtained by dissolving the coloured species in a solvent and measuring the intensity and wavelength of the light absorbing species using a colorimeter or spectrophotometer.

Therefore, in one embodiment of this invention, the coloured reaction product is caused to form a solution in a solvent and then the visible colour and/or colorimetric absorbance of said solution is related to the presence and/or amount of the unstable compounds in the oil.

This solvent is preferably at least partly organic, wholly or partly immiscible with the oil, and consequently the colour and/or absorbance may be observed in the separate solution phase. It is also preferred in this embodiment that the acid catalyst is soluble in the solvent. Preferably the solvent is a polar solvent substantially immiscible with the oil, and is a water-miscible organic solvent or an organic solvent-water mixture. Preferred solvents are therefore alcohols, especially lower alcohols (i.e. up to $C_5$ alcohols), especially methanol or ethanol, or mixtures of these with water. The use of a solvent, particularly methanol, conveniently allows the acid catalyst to be added to the oil in the form of a solution in the solvent. The acid catalyst/polar solvent is preferably added to the oil at a fuel/solvent ratio from 20:1 to 1:4 volume/volume. The intensity of the colour which develops with the unstable oil is then determined in the solvent layer, by visual observation or by absorbance measurement. In this embodiment the method may be carried out at ambient temperature but is preferably carried out at an elevated temperature, e.g. 20°–50° C.

The appearance of a blue, green or blue-green colour in the solvent visible to the naked eye, or which may be detected by a colorimetric instrument at a wavelength between 600–850 nm, is associated with potential instability of the oil. The intensity of the colour, and/or wavelength of the colorimetric absorption maximum may be related to the amount of sediment which is expected to form, and hence to a storage lifetime or acceptability relative to a quality control standard.

In an alternative form of this embodiment a solid acid catalyst is contacted with the oil, a coloured reaction product is allowed to form on the surface of the catalyst, the oil and catalyst are separated, e.g. by decantation, and the solution is formed, e.g. by addition of the solvent to the solid catalyst. Preferred solid catalysts are para-toluene sulphonic acid or naphthalene sulphonic acid, and a preferred solvent is methanol.

In a second embodiment of this method an oxidising agent is also contacted with the oil, together with the acid. The use of an additional oxidising agent is believed to assist in causing the oxidation of phenalenes to phenalenone and phenalanones. In this embodiment it is also preferred that the coloured reaction product is caused to form a solution as described in the first embodiment above and therefore the preferred features of this first embodiment are included in this second embodiment.

Any oxidising agent which is known to oxidise phenalenes to phenalenones may be used. Inorganic oxidising agents are preferred, particularly transition metals in an oxidising oxidation state such as Ce IV, Mn VII (e.g. permanganate) or Cr VI (e.g. dichromate). These latter two give a rapid reaction without interference from the colour of the reduced ion. Other suitable oxidising agents include $I_2$, $IO_3^-$, $BrO_3^-$ and $C_{10}^-$. $H_2O_2$ may also be used but can give a slower reaction.

It is particularly preferred to carry out this second embodiment of the method by contacting the oil with an oxidising agent, an acid, and a solvent which is at least partly organic and which is wholly or partially immiscible with the oil, said oxidising agent and acid being at least partly soluble in the solvent, then observing the colour of the solvent phase, either visually or by measuring the absorbance.

Some acids are also oxidising agents, such as perchloric and nitric acids. Such oxidising acids may therefore in some cases be used in place of both the oxidising agent and the acid, or may be used in addition to either or both. Perchloric and nitric acids may for example be used as both an acid and oxidising agent or may be used together with an additional oxidising agent such as dichromate.

It is preferred to provide the oxidising agent as a solution, especially when the acid catalyst is also provided as a solution. These solutions may both be made up in the same selected solvent, or if the solvent is a water-miscible organic liquid or an organic liquid-water mixture one may be made up in this and the other in water. In this way all the materials used in the test method may then conveniently be added as these two solutions.

When an oxidising agent is used, a preferred solvent is a methanol- or ethanol- water mixture solvent, preferably containing 70–80% by volume of the alcohol. This mixture dissolves around 2–3 weight % of potassium dichromate or permanganate. When the acid is provided in the form of a solution then this preferably contains 10% or less by weight of the acid. When the oxidising agent is a compound of a transition metal and is provided as a solution then this is preferably a saturated solution, especially when in water so that the minimum volume of water need be used in the method.

In use in a preferred form of this second embodiment, a sample of the oil is taken and to it is added the oxidising agent, acid and solvent. The mixture is then preferably agitated so as to bring all the ingredients into intimate physical contact. The mixture is then preferably allowed to separate into the solvent phase and the oil phase, and then the colour of the solvent phase is observed. When the oxidising agent and acid are added as one or more solutions, it or these may be added to the sample of the oil, forming the solvent phase which separates from the oil.

When an oxidising agent is used as described above, the test method may be used with small samples of the oil, at ambient temperature. The test takes overall around 5–10 minutes, most of which time is spent waiting for the solvent and oil phases to separate, and can detect as little as 1–2 ppm of phenalenes or phenalenones. The quantities of the oxidising agent and acid do not appear to be critical but very dilute reagents can lead to a slow production of a result. For consistency, it is important to use as far as possible the same conditions for each test. Conveniently a sample of about 5 ml of the oil may be used, to which need be added no more than about 0.5–2 ml of solvent. When the acid and oxidising agents are in separate solutions, e.g. the preferred solutions described above, then typically 0.5 ml of the acid solution and 1 drop to 0.5 ml of the oxidising agent need be used.

In the above two embodiments, the rate and intensity of colour development may be enhanced by carrying out the method in the presence of a solid material, preferably a white material. Preferred solid materials are silica, e.g. chromotographic silica, silicaceous earths such as Kieselgel G, and calcium sulphate.

The solid material may be simply added to the mixture of oil, acid, and if present, solvent and oxidising agent, or in a preferred form it may be mixed with the acid catalyst prior to addition of the oil. In such a mixture the catalyst is preferably present in concentrations of 0.1% to 10% by weight. Preferred mixtures are of chromotographic silica, silicaceous earth or calcium sulphate with solid para-toluene sulphonic acid. Alternatively the solid material/catalyst mixture may comprise a silica substrate having a sulphonic acid chemically bonded thereto, for example as commercially available strong cation exchange media where acids such as benzene sulphonic and propyl sulphonic are chemically bonded to silica. One such material containing benzene sulphonic acid is sold under the trade mark BOND-ELUT SCX.

The solid material may physically support the acid catalyst. It may act as a background to the colour or it may absorb the coloured product. In this latter situation the support may be allowed to settle, then be separated from the oil, and the coloured product washed from the support into solution with a solvent.

Preferably the oil:solid material ratio is in the range of 1:1 to 500:1 by volume if it is added into the mixture as described above.

In the above descriptions the mixture of materials with the oil and each other may be carried out in any order or simultaneously.

In a third embodiment of this method the solid material/acid catalyst mixture is provided in the form of a column through which the oil is allowed to pass, or in the form of a layer on a solid backing along which the oil is allowed to flow. The flow may be in a manner analogous to a TLC plate or the layer and backing may be dipped into or otherwise coated with the oil or a solution of the oil and allowed to drain. Preferred acid catalysts, solid supports and mixtures thereof are as discussed above.

Short columns may be used, e.g. 10 mm long by 5 mm diameter, requiring only 5 ml of the oil. In such a column the support material is preferably in the form of a powder, especially 100–200 mesh size. In both columns and layers the concentration of the acid catalyst in the mixture may vary along the length of the column or across a dimension, e.g. length, of the layer.

When such columns and layers are used, the coloured product imparts a visible blue or blue-green colour to the column or layer which may be related to the presence and/or amount of unstable compounds in the oil. Alternatively the coloured product may be caused to form a solution in a solvent such as methanol by elution from the column with the solvent, the visible colour or colorimetric absorbance of which may be observed and related to the presence and/or amount of unstable compounds in the oil.

In this third embodiment the intensity of the colouration on the column or layer may be enhanced by adding an oxidising agent to the oil prior to passing it through the column or contacting the layer with it. Preferred oxidising agents are as discussed above with reference to the second embodiment, but hydrogen peroxide is particularly preferred. The oxidising agent may be added to the oil neat or in solution in a solvent.

A fourth embodiment is to pass the oil through a column of solid support material which retains the unstable compounds from the oil. Chromatographic silica, 100–200 mesh size, is a preferred support material. The unstable compounds are then removed from the column by washing with a polar solvent, methanol being preferred. The addition of an acid catalyst to the methanol washings then imparts a blue or blue-green colour, the visible colour or colorimetric absorbance of which may be observed and related to the presence and/or amount of unstable compounds in the oil. Similar columns and similar amounts of materials to those described in relation to the third embodiment may be used.

For convenience test kits may be provided containing in combination the materials and reagents necessary for performing the test method of this invention. For example a test kit for performing the first embodiment may include a solution of an acid catalyst in a suitable solvent. For performing the second embodiment the test kit may include separate solutions of an acid catalyst and an oxidising agent in suitable solvents. The kits for the first and second embodiments may also include a powdered solid support material which may be prior mixed with the acid catalyst, and solvent. For performing the third embodiment the kit may include a ready made column, or layer on a backing, of a support/acid mixture, a solvent, and an oxidising agent. The kits may also include suitable vessels for performing the test, and/or colour comparison charts.

Non-limiting examples illustrating the invention follow.

Figure 1:
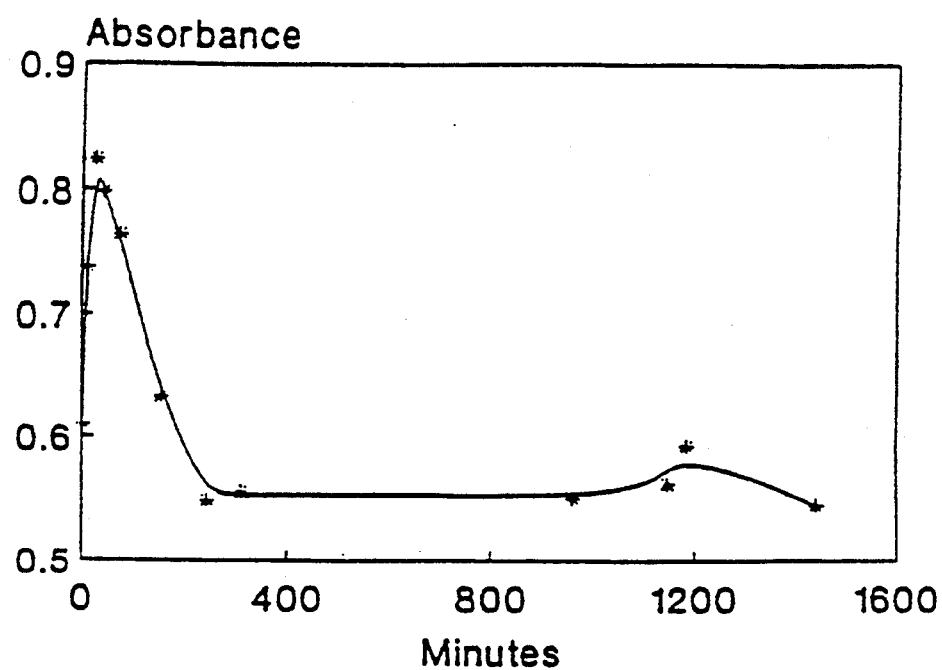
FIG. 1 shows colour development with time on a column.

The following reference fuels, on which comparative studies have been carried out, are referred to:

Fuel A: Straight run automotive distillate from Refinery 1.
Fuel B: Straight run automotive distillate from Refinery 2.
HCCLCO: Hydrogenated catalytically cracked light cycle oil.
TCLCO: Thermally cracked light cycle oil.
CCLCO: Catalytically cracked light cycle oil.
Fuel C: Blend of 30% HCCLCO with Fuel B.
Fuel D: Blend of 5% TCLCO with Fuel A.
Fuel E: Blend of 5% CCLCO with Fuel B.
Fuel F: Blend of 30% TCLCO with Fuel A.
Fuel G: Blend of 30% CCLCO with Fuel B.

The relative stability of each of the reference fuels was determined using the method of DEF STAN 05-50 (Part 40/1—long method). The amount of insoluble matter formed on ageing is shown in the Table.

| FUEL | TOTAL INSOLUBLE mg/l |
|---|---|
| Fuel A | 5 |
| Fuel B | 4 |
| Fuel C | 3 |
| Fuel D | 13 |
| Fuel E | 9 |
| Fuel F | 54 |
| Fuel G | 43 |

Fuels D, E, F and G are considered unstable.

EXAMPLE 1

Ten drops of one of the following liquid catalysts or 20 mg of one of the solid catalysts: concentrated hydrochloric acid, concentrated sulphuric acid, benzoyl chloride, para-toluene sulphonic acid, naphthalene sulphonic acid, dodecylbenzene sulphonic acid; were dissolved in 20 ml of methanol and added to 50 ml of each reference fuel. The methanol is not fully miscible with the fuels and a two phase mixture was formed. The mixture was vigourously shaken after mixing the catalyst and again after 23 hours at 43° C. After standing for a further hour at 43° C., no blue colouration was apparent in the methanol layer with the stable Fuels A–C, a pale blue colouration was apparent with unstable Fuels D and E and a darker blue colouration with F and G.

Detection of the blue colouration was quantified by measurement of the light absorbance of the methanol layer in the region 600 to 850 nanometers using a ultraviolet/visible spectrophotometer. The absorbance of the methanol layers from the stable Fuels A–C at 770 nanometers in a 1 cm pathlength cell was less than 0.01. The absorbance readings for the unstable fuels at this wavelength were as follows: D, 0.37; E, 0.23; F, 1.76; G, 1.48.

The intensity of the blue colour increased with increasing temperature of the fuel/methanol/catalyst mixture and with time beyond the 24 hours.

EXAMPLE 2

Solid crystals of para-toluene sulphonic acid or o naphthalene sulphonic acid were added to fuel. A dark blue colouration was produced on undissolved solid after 24 hours standing at 43° C. with the unstable fuels. This blue colouration was readily seen by decanting the fuel and adding 5 ml of methanol to the solid residue. No blue colouration was observed in the methanol solution with the stable fuels, a medium colouration was obtained with unstable Fuels D and E and a dark blue colouration with unstable Fuels F and G.

EXAMPLE 3

Oxidising Agent: Saturated solution of potassium dichromate or potassium permanganate in water or of potassium dichromate in aqueous methanol (70–80% v:v methanol).

Acid/Organic Solvent: Solution of p-toluene sulphonic acid in methanol (10 wt %).

Approximately 5 ml of a diesel fuel were placed in a 10 ml graduated test tube. 0.5 ml of the acid solution was added followed by one drop of the oxidising agent solution. The tube was stoppered and the mixture was vigorously shaken for one minute then allowed to stand until two distinct layers had formed, the methanolic layer being uppermost. This took 5–10 minutes. The colour of the methanolic layer was observed and recorded by a colour photograph.

This method was applied to 5 samples of diesel oil of decreasing long term storage stability in respect to sediment formation. These were (1) straight run ("SR") gas oil (known to be stable); (2), (3), (4) and (5) respectively 0.1%, 1%, 5% and 10% catalytically cracked blend in SR gas oil. Samples (4) and (5) produced a deep green colouration of the methanolic phase which was found to represent an unacceptable level of sediment formation on storage. With samples (1) and (2) no green colouration at all was visible to the naked eye, and in sample (3) a green ring was visible at the junction between the oil and solvent layers but no green colouration was visible to the naked eye in the solvent phase itself. Samples (1) and (2) in which no hint of green colouration was visible to the naked eye, were also tested by present standard tests for diesel oil and found to have an acceptable level of storage stability to a UK Ministry of Defence Standard requiring long term formation of no more than 2 mg of sediment per 100 g of fuel on storage whilst samples (3), (4) and (5) when tested by the present standard test were found to yield an unacceptable amount of sediment by this MOD standard.

EXAMPLE 4

Solid para-toluenesulphonic acid (0.1 g) was ground with 100–200 mesh chromatographic silica (10 g) and the powder added to a 5 mm diameter glass or plastic tube to a height of 10 mm above a plug of glass wool to retain the powder. Each fuel (1.0 ml) was added to a separate tube above the silica. The fuel was allowed to percolate through the powder under gravity. With unstable Fuels F and G, medium green/blue colourations were produced in the silica within one minute of addition of the fuel. Within 5 minutes no fuel remained above the silica and the medium green/blue colouration was spread throughout the silica. A lighter green/blue colouration was similarly produced with unstable Fuels D and E, while no colouration was produced with the stable Fuels A, B and C.

EXAMPLE 5

Separate tubes containing silica were similarly prepared (10 g of silica ground with 0.1 g of acid catalyst) with each of the following acidic catalysts: naphthalene sulphonic acid, dodecylbenzene sulphonic acid, concentrated hydrochloric acid (37%), concentrated sulphuric acid (98%), benzoyl chloride, and acetyl chloride. Addition of unstable Fuels F and C (1 ml) to all tubes produced in each case a green/blue colouration in the silica within 1 minute of addition of the fuel. Within 5 minutes the fuel had percolated through the silica and green/blue colour was evident throughout the column. With the unstable Fuels D and E the colour was less intense, while the green/blue colour was absent with each of the stable fuels, A, B and C.

EXAMPLE 6

The TCLCO and CCLCO, blended to produce the unstable fuels used in the tests described above, were frozen at −15° C. within seven days of being obtained from the refinery. A further series of unstable fuels was prepared with the same proportion of TCLCO and CCLCO, but using TCLCO and CCLCO which had been standing at ambient temperatures for three months. Blue/green colour development was observed within 5 minutes on the treated silica tubes for those fuels containing the freeze-stored LCO. However, with the three ambient aged LCO blends a dark blue band was formed at the top of the silica column and there was less intense blue/green colouration throughout the silica. The intensity of the dark blue band at the top of the silica column was an indication of the age of the LCO in the unstable fuel blend.

EXAMPLE 7

Variations of the method of addition of the acidic catalysts to the solid silica were to dissolve the material in a solvent. For example, para-toluene sulphonic acid (0.1 g) was dissolved in methanol (10 ml) and a slurry formed with the silica. The methanol solvent was removed by evaporation with gentle heating and the column prepared from the dried silica as previously. Alternatively, the column could be packed with untreated silica and methanol/acid catalyst (0.5 ml) added above the silica. Gentle heating of the column was then sufficient to evaporate the methanol. In all cases with columns prepared with these variants, blue/green colouration was produced with the unstable Fuels D–G and not with the stable Fuels A–C. The intensity of the colouration was proportional to the amount of acid remaining on the column. This could be varied by the initial concentration in the solvent, by the amount of solvent added to the column and by the number of solvent additions.

EXAMPLE 8

Columns were also prepared in which the amount of acid catalyst varied along the length of the column. For example, para-toluene sulphonic acid (0.1 g) was dissolved in a mixed isopropanol/toluene solvent (1:4 by volume). The solvent/acid catalyst (1 ml) was added to the silica column followed by 2 ml of hexane. After allowing the column to air dry, 1 ml of each of the test fuels was added to individual columns in a counter direction to that of addition of the solvent/acid catalyst. With each of the unstable fuels, a graduation of blue/green colour was obtained from the top (where the fuel was added) to the bottom of the column, with the darkest colouration being at the bottom corresponding to the highest catalyst concentration. Variations of intensity of colour were readily seen by comparison of the colour graduation for tubes from each of the unstable fuels D–G. The intensity of the colour was proportional to the amount of sediment produced in the fuel as listed in the Table above.

EXAMPLE 9

Acid catalyst was also deposited on a "thin layer" coating of silica on a flexible polymer backing plate from a methanol (5 ml)/acid catalyst (0.1 g) solution. In this case, the flexible polymer plate and silica coating was immersed into the acidic solution and removed after all the silica coating was fully wetted with solvent.

The methanol solvent was allowed to air evaporate to leave residual acid catalyst. The treated "thin layer" plate was immersed into the test fuel until the silica layer was fully wetted with the fuel and then withdrawn. As previously, the intensity of the blue/green colouration produced on the silica coating was proportional to the amount of sediment produced in the unstable fuels.

EXAMPLE 10

A variation of this coating procedure was to apply successive coatings of residual acid catalyst to portions of the plate. As an example, the complete silica coating of the plate was wetted with the acid catalyst/methanol (ACM) solution, and the methanol solvent allowed to evaporate. Then 80% of the silica coating was wetted with a second AMC solution followed by air evaporation of the solvent. This was similarly followed by 60% (three ACM wettings), 40% (four ACM wettings) and 20% (five ACM wettings) of the silica surface being wetted with acid catalyst/methanol solvent. The five concentration variations of acid catalyst were obtained along the silica plate corresponding to the number of wettings with ACM solution. When this plate was immersed into the unstable fuels and withdrawn after being wetted with fuel, a blue/green colouration was again obtained, which was proportional to the amount of acid catalyst deposition on the silica and the amount of deposit produced in the fuel.

EXAMPLE 11

In addition to the columns produced with silica, Kieselgel G, and anhydrous calcium sulphate were used as solid supports for the acid catalysts applied as described above. Blue/green colourations were again obtained on the solids with the unstable fuels, although the relative intensities of the colours were not as great as with the silica support and the relative distribution through the solids was not as even.

EXAMPLE 12

Two Fuel D samples were added to a silica/para-toluene sulphonic acid catalyst column. The first such sample was Fuel D prepared as above. In the second sample, one drop of 100 volume hydrogen peroxide was added to 1 ml of Fuel D and the mixture was allowed to stand at ambient temperature for 60 minutes before addition to the column. The intensity of the blue/green colouration in the column was greater with the sample containing hydrogen peroxide. Other oxidising agents similarly produced an enhancement of the colouration.

EXAMPLE 13

The colour produced in the solid columns was quantified by passing methanol (2 ml) after all the fuel had passed through the column and measurement of the intensity of the colour extracted into the methanol in the range 600 to 850 nanometers. For example, following washing with methanol (2 ml) 60 minutes after passage of unstable fuels D and F (1 ml) through silica/-para-toluene sulphonic acid catalyst column, absorbances at 770 nanometers of 0.11 and 0.29 respectively were obtained in a 10 mm pathlength cell.

EXAMPLE 14

A 4 cm long Column of the silica-p-toluene sulphonic acid mixture used in Example 4 was made in a 5 mm diameter clear glass tube. A syringe was used to add 2 ml of fuel oil to the tube. Gentle pressure was applied to cause the oil to flow through in 30 seconds. Colour development occurred immediately and in most cases was complete within 10 minutes.

Spectral measurements were obtained after washing the column with 1 ml of hexane to remove residual oil, followed by 6 ml of methanol. In each case gentle pressure was applied to cause the liquid to flow through in 30 seconds Spectra of the methanol wash liquid were recorded immediately using 10 mm pathlength cells.

Figure 2:
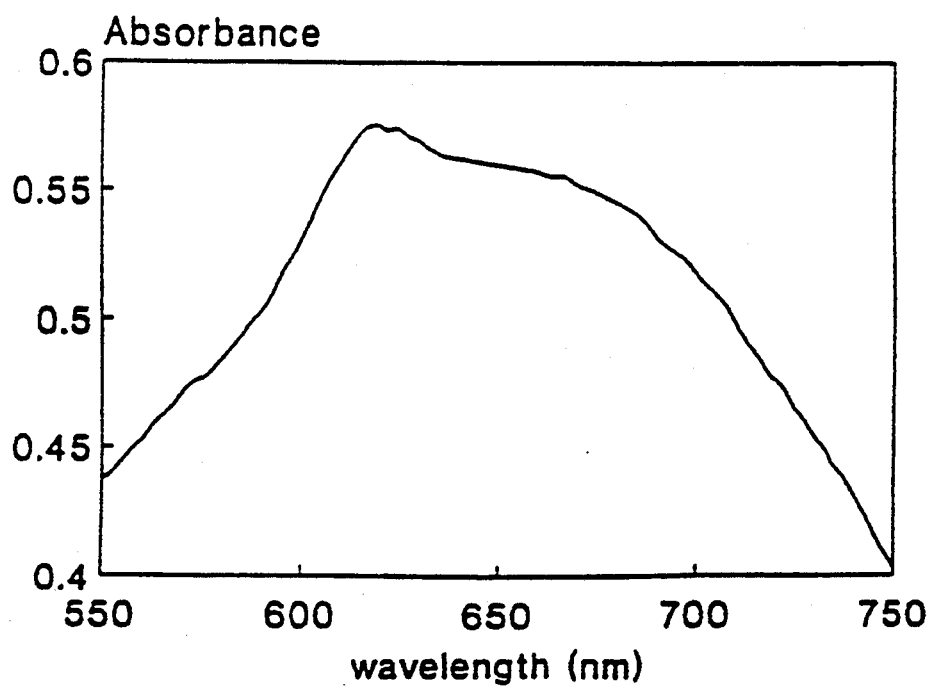
FIG. 2 shows the spectrum of coloured reaction product in methanol.

FIG. 1 shows the rapidity of colour development. Columns were washed after period of 2–1500 minutes following addition of 2 ml of fuel oil containing 15% of light cycle oil (LCO) obtained directly from Australian refineries within one week of production. From 300 to 1400 minutes at ambient temperature the absorbance of 650 nm was relatively constant. FIG. 2 shows the spectrum of column methanol washings after 300 minutes.

Figure 3:
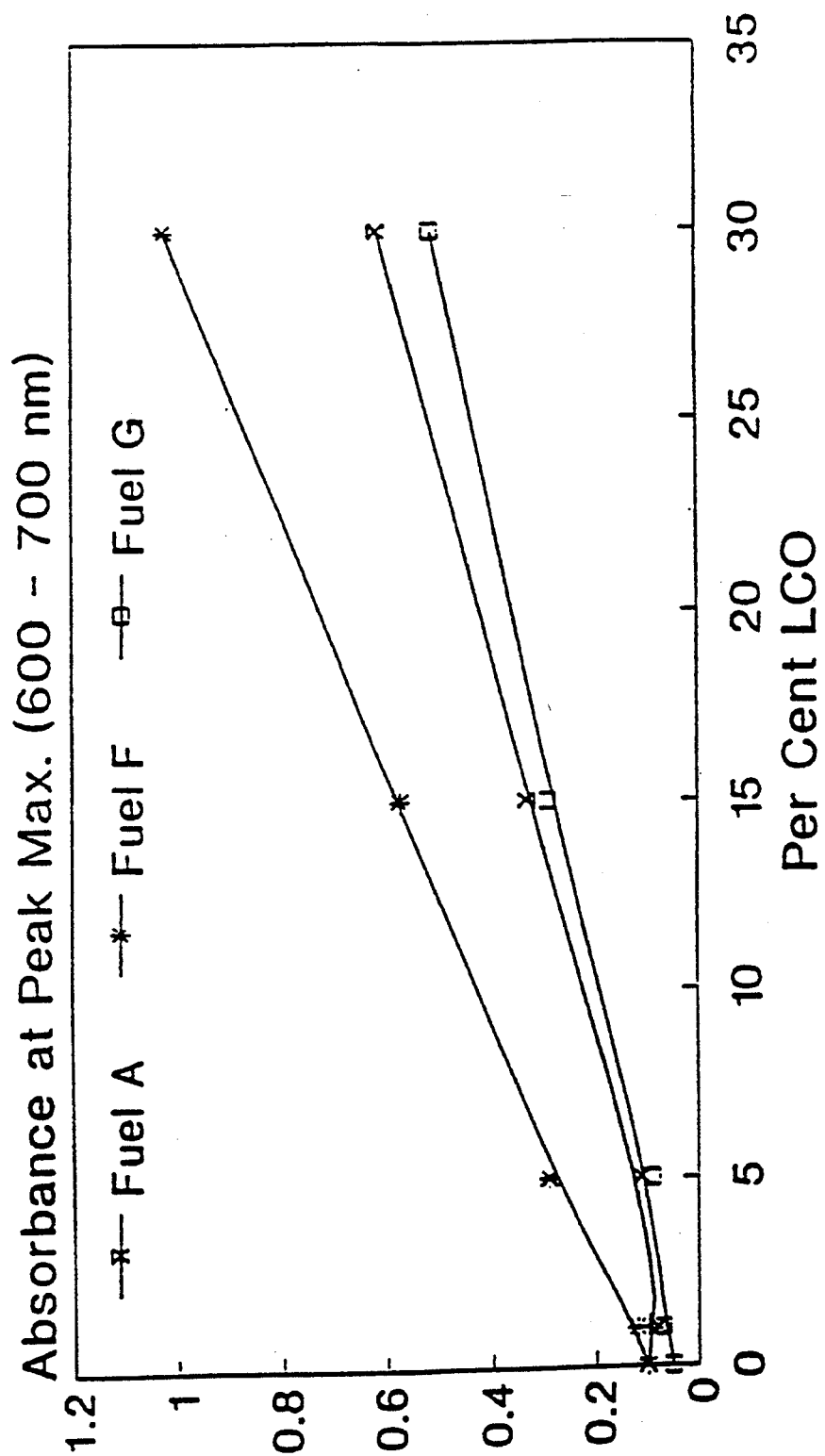
FIG. 3 shows the relationship between colorimetric absorbance and light cycle oil content in three fuel oil samples.

Results from 5 blends of LCO from 3 refineries are shown in FIG. 3. The variation of absorbance with LCO concentration was approximately linear from 0 to 30% LCO content.

EXAMPLE 15

A 4 cm long column of chromatographic silica (100–200 mesh) was prepared in a 5 mm diameter glass tube. A plastic tube was used to add 2 ml of fuel oil to the tube. Gentle pressure was applied to cause the oil to flow through in 30 seconds.

The column was washed with 1 ml of hexane followed by 6 ml of methanol. Two ml of a 10% solution of p-toluene sulphonic acid in methanol was added to the methanol washings and the resultant colour noted and its absorbance in the 600–850 nm region measured between one and 16 hours after the acid addition.

Comparison of results from ASTM D4625 and oxygen overpressure tests with the method of the invention showed that fuels producing the most sediment also produced the highest absorbance.

LCO has a high aromatic content and also is a better solvent than straight run distillate (SRD) for potential sediment forming materials, which can consequently form injector and cylinder deposits. The test method of the invention easily allows the amount of LCO in a fuel oil to be determined.

We claim:

1. A method of testing a fossil-fuel derived hydrocarbon oil containing an indole for the presence of chemically unstable compounds selected from the group consisting of phenalenes, phenalanones and phenalenones, wherein a sample of the oil is contracted with a Lowry-Bronsted acid catalyst to form a colored reaction product between the indole and the unstable compound when present in the sample; and the color of the sample within the region between 600–850 nm is visually observed and the presence of at least one of said unstable compounds in said sample is determined by comparison to a predetermined standard.

2. A method according to claim 1, wherein the acid catalyst is selected from the group consisting of: mineral acids, carboxylic acids, aryl or alkyl sulphonic acids, aryl or alkyl acyl chlorides, and aryl or alkyl acid anhydrides.

3. A method according to claim 1 wherein the colored reaction product is brought into solution in a solvent which is at least partly organic and is at least partly immiscible with the oil prior to relating the visible color of the reaction product to the amount of named unstable compound in the oil.

4. A method according to claim 3 wherein the intensity of visible color is observed in the solution phase and the acid catalyst is soluble in the solvent.

5. A method according to claim 4 wherein the solvent is selected from the group consisting of $C_1$ to $C_5$ alcohols and mixtures of such alcohols with water.

6. A method according to claim 4 wherein a solution of the acid catalyst in the solvent is contacted with the oil.

7. A method according to claim 4 wherein: the acid catalyst is a solid; colored reaction product forms on the surface of the catalyst; the oil and catalyst are separated; and, the solution is thereafter formed.

8. A method according to claim 1 wherein an oxidizing agent capable of converting a phenalene to a phenalenone is contacted with the sample.

9. A method according to claim 8 wherein to the oil are added: the oxidizing agent; acid catalyst; and, a solvent selected from the group consisting of $C_1$ to $C_5$ alcohols and mixtures of such alcohols with water, and which is wholly or partially immiscible with the oil; said oxidizing agent and acid catalyst being at least partly soluble in the solvent: and, wherein the color of the solvent phase is then visually observed.

10. A method according to claim 9 wherein a solution of the oxidizing agent in the solvent is contacted with the sample.

11. A method according to claim 10 wherein a solution of the acid in the solvent is contacted with the sample.

12. A method according to claim 1 wherein: the sample; acid catalyst; and an optional solvent selected from the group consisting of $C_1$ to $C_5$ alcohols and mixtures of such alcohols with water; and an oxidizing agent capable of converting a phenalene to a phenalenone, are contacted in the presence of a solid support material.

13. A method according to claim 12 wherein the solid support material is mixed with the acid catalyst prior to contact with the sample.

14. A method according to claim 13 wherein the mixture of solid support material and acid catalyst contains 0.1 to 10 weight % of the acid catalyst.

15. A method according to claim 13 wherein the acid catalyst plus support material mixture is provided in the form of a column through which the oil sample is passed.

16. A method according to claim 15 wherein the colored reaction product is eluted from the column with a solvent to form a solution.

17. A method according to claim 15 wherein the concentration of acid catalyst in the acid catalyst plus support mixture varies along the length of the column.

18. A method according to claim 15 wherein the oil is treated with oxidizing agent prior to causing it to flow through the column.

19. A method according to claim 13 wherein the acid catalyst plus support mixture is provided in the form of a layer on a solid backing, over which layer said sample is allowed to flow.

20. A method according to claim 19 wherein the concentration of acid catalyst in the acid catalyst plus support mixture varies over a dimension of the layer.

21. A method according to claim 19 wherein the oil is treated with oxidizing agent prior to causing it to flow over the layer.

22. A method according to claim 1 wherein reactive compound is separated from the oil before unstable compound is contacted with the acid catalyst.

23. A test kit for performing a method according to claim 1 and including a Lowry-Bronsted acid catalyst supported by a solid material, an oxidizing agent capable of converting a phenalene to a phenalenone, and a color comparison chart having a range of color absorption intensities in the region 600–850 nm.

24. A test kit according to claim 23 wherein the catalyst and supporting solid material is in the form of an enclosed column.

25. A test kit according to claim 23 wherein the catalyst and supporting solid material is laid on a solid backing.

26. A test kit for performing a method according to claim 1 and including a Lowry-Bronsted acid catalyst, a solvent selected from the group consisting of $C_1$ to $C_5$ alcohols and mixtures of such alcohols with water, an oxidizing agent capable of converting a phenalene to a phenalenone, and a chart enabling comparison of spectrometric test results with spectrometric results on predetermined standard materials in the region 600–850 nm.

27. A method according to claim 9, wherein intensity of color of the solvent phase is visually estimated against a chart standard.

28. A method according to claim 9, wherein intensity of color of the solvent phase is measured in the visible spectrum in the range 600–850 nm.

29. A method according to claim 1, further including a step of measuring intensity of color of the solvent phase.

30. A method according to claim 29, wherein intensity of color of the solvent phase is measured by using a colorimeter or spectrophotometer.

* * * * *

UNITED STATES PATENT AND TRADEMARK OFFICE
CERTIFICATE OF CORRECTION

PATENT NO. : 5,378,632

DATED : January 3, 1995

INVENTOR(S) : Richard K. Solly; Alan J. Power; Ludek A. Beranek; Shiela J. Marshman; Joanna F. Pedley; Robin W. Hiley It is certified that error appears in the above-identified patent and that said Letters Patent is hereby corrected as shown below:

Section (75), Inventors, after the name "Pedley," delete --Walton on Thames,--.

Section (75), Inventors, after the name "Pedley," insert --Surrey,--.

Section (75), Inventors, after the name "Hiley," delete --Sevenoaks,--.

Section (75), Inventors, after the name "Hiley," nsert --Kent,--.

Column 2, line 31, delete "believer" and insert therefor --believed--.

Column 8, line 55, after the word "or" delete --o--.

Column 11, line 66, delete "Column" and insert therefor --column--.

Column 12, line 52, delete "contracted" and insert therefor --contacted--.

Column 14, lines 48 and 49, after the word "color", delete --of the solvent phase--.

Column 14, line 51, after the word "color", delete --of the solvent phase--.

Signed and Sealed this

Twelfth Day of September, 1995

Attest:

BRUCE LEHMAN

Attesting Officer   Commissioner of Patents and Trademarks